(12) United States Patent
Cohen

(10) Patent No.: US 9,357,966 B1
(45) Date of Patent: *Jun. 7, 2016

(54) DRUG SCREENING DEVICE FOR MONITORING PUPIL REACTIVITY AND VOLUNTARY AND INVOLUNTARY EYE MUSCLE FUNCTION

(71) Applicant: Karen Elise Cohen, Smyrna, GA (US)

(72) Inventor: Karen Elise Cohen, Smyrna, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/722,107

(22) Filed: May 26, 2015

Related U.S. Application Data

(60) Provisional application No. 62/093,559, filed on Dec. 18, 2014.

(51) Int. Cl.
*A61B 5/00* (2006.01)
*A61B 3/113* (2006.01)
*A61B 3/11* (2006.01)

(52) U.S. Cl.
CPC .............. *A61B 5/4845* (2013.01); *A61B 3/112* (2013.01); *A61B 3/113* (2013.01); *A61B 5/4058* (2013.01); *A61B 5/4863* (2013.01); *A61B 5/6803* (2013.01)

(58) Field of Classification Search
None
See application file for complete search history.

(56) References Cited

U.S. PATENT DOCUMENTS

| 7,448,753 | B1 * | 11/2008 | Chinnock | A61B 3/14 351/206 |
| 2007/0236663 | A1 * | 10/2007 | Waldorf | A61B 3/112 351/206 |
| 2011/0085135 | A1 * | 4/2011 | Bertolli | A61B 3/113 351/206 |
| 2014/0313488 | A1 * | 10/2014 | Kiderman | A61B 3/145 351/246 |
| 2015/0085252 | A1 * | 3/2015 | Fujimura | A61B 3/15 351/208 |

OTHER PUBLICATIONS

Meunier et al. "A Video-Based Image Processing System for the Automatic Implementation of the Eye Involuntary Reflexes Measurements Involved in the Drug Recognition Expert (DRE)." IEEE/ACS International Conference on Computer Systems and Applications, Mar. 31, 2008, pp. 599-605.*

Iijima et al. "Head Mounted Goggle System with Liquid Crystal Display for Evaluation of Eye Tracking Functions on Neurological Disease Patients." Proceedings of the 25th Annual International Conference of the IEEE, vol. 4, Sep. 17, 2003, pp. 3225-3228.*

* cited by examiner

*Primary Examiner* — Jon Chang
(74) *Attorney, Agent, or Firm* — Buskop Law Group, PC; Wendy Buskop

(57) ABSTRACT

A drug screening device for testing an iris for use of a chemical known to have a neurological effect that interferes with normal functioning of the iris and the voluntary muscles of the eye. The drug screening device can test and document reactivity of the iris under known light conditions and can test for the presence of horizontal nystagmus. The identity of a subject can be confirmed by applying an iris pattern recognition model of a captured image of an iris of the eye compared with an image of an iris stored in a library of baseline color or a library of infrared eye images. The device can provide alarms when one eye pupil diameter exceeds or falls below the opposite eye pupil diameter and when horizontal gaze nystagmus has been determined to be present.

8 Claims, 10 Drawing Sheets

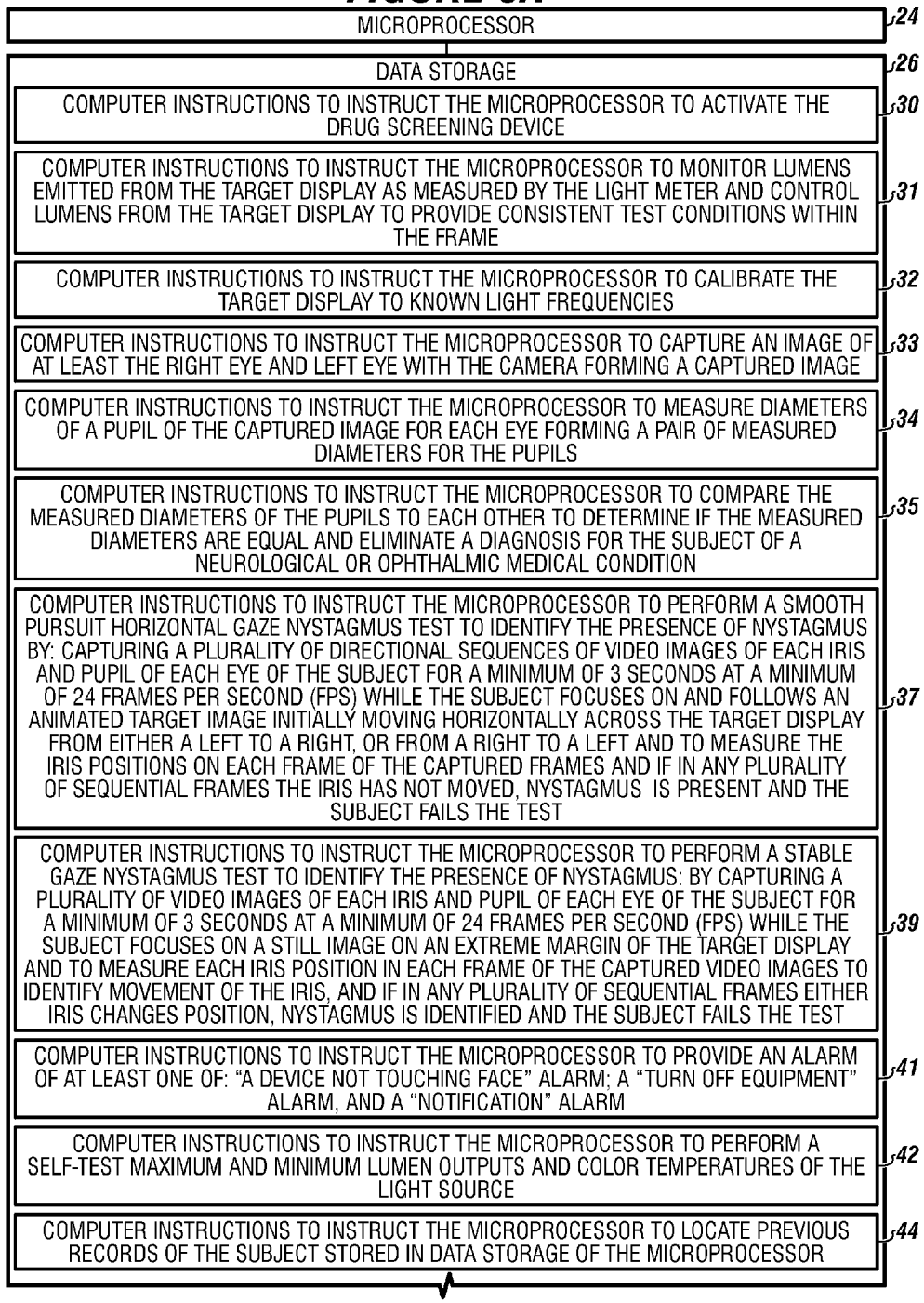

| 26
| COMPUTER INSTRUCTIONS TO INSTRUCT THE MICROPROCESSOR TO INCREASE OR DECREASE LIGHT OUTPUT FROM THE LIGHT SOURCE AND/OR TARGET DISPLAY TO A LUMEN LEVEL OF A PREVIOUS IRIS SCAN OF THE SUBJECT STORED IN A DATA STORAGE OF THE MICROPROCESSOR | 50 |

| | |
|---|---|
| MONITORING LUMEN OUTPUT EMITTED FROM THE TARGET DISPLAY AS MEASURED BY THE LIGHT METER AND CONTROL LUMEN OUTPUT FROM THE TARGET DISPLAY TO PROVIDE CONSISTENT TEST CONDITIONS WITHIN THE FRAME | 200 |
| CAPTURING AN IMAGE OF AT LEAST A RIGHT EYE AND A LEFT EYE WITH A CAMERA FORMING A CAPTURED IMAGE | 202 |
| MEASURING DIAMETERS OF A PUPIL OF THE CAPTURED IMAGE FOR EACH EYE FORMING A PAIR OF MEASURED DIAMETERS FOR THE PUPILS | 204 |
| COMPARING THE MEASURED DIAMETERS OF THE PUPILS TO EACH OTHER TO DETERMINE IF THE MEASURED DIAMETERS ARE EQUAL AND ELIMINATE A DIAGNOSIS FOR THE SUBJECT OF A NEUROLOGICAL OR OPHTHALMIC MEDICAL CONDITION | 206 |
| APPLING A PATTERN RECOGNITION MODEL TO THE CAPTURED IMAGE AND MATCH AN IRIS OF THE EYE OF THE CAPTURED IMAGE TO A STORED IMAGE OF THE EYE TO CONFIRM AN IDENTITY OF THE SUBJECT, THE STORED IMAGE OF THE EYE RETRIEVED FROM AT LEAST ONE IMAGE OF: A LIBRARY OF BASELINE COLOR EYE IMAGES OF THE SUBJECT ACCESSIBLE BY THE MICROPROCESSOR THROUGH A NETWORK; A LIBRARY OF BASELINE INFRARED EYE IMAGES OF THE SUBJECT ACCESSIBLE BY THE MICROPROCESSOR THROUGH A NETWORK | 209 |
| PERFORMING A HORIZONTAL GAZE NYSTAGMUS TEST TO IDENTIFY THE PRESENCE OF NYSTAGMUS BY: CAPTURING A PLURALITY OF DIRECTIONAL SEQUENCES OF VIDEO IMAGES OF EACH IRIS AND PUPIL OF EACH EYE OF THE SUBJECT FOR A MINIMUM OF 3 SECONDS AT A MINIMUM OF 24 FRAMES PER SECOND (FPS) WHILE THE SUBJECT FOCUSES ON AND FOLLOWS AN ANIMATED TARGET IMAGE INITIALLY MOVING HORIZONTALLY ACROSS THE TARGET DISPLAY FROM EITHER A LEFT TO A RIGHT, OR FROM A RIGHT TO A LEFT | 211 |
| MEASURING THE IRIS POSITIONS ON EACH FRAME OF THE CAPTURED FRAMES AND IF IN ANY PLURALITY OF SEQUENTIAL FRAMES THE IRIS HAS NOT MOVED, NYSTAGMUS IS PRESENT AND THE SUBJECT FAILS THE TEST | 213 |
| PERFORMING A STABLE GAZE NYSTAGMUS TEST TO IDENTIFY THE PRESENCE OF NYSTAGMUS: BY CAPTURING A PLURALITY OF VIDEO IMAGES OF EACH IRIS AND PUPIL OF EACH EYE OF THE SUBJECT FOR A MINIMUM OF 3 SECONDS AT A MINIMUM OF 24 FRAMES PER SECOND (FPS) WHILE THE SUBJECT FOCUSES ON A STILL IMAGE ON AN EXTREME MARGIN OF THE TARGET DISPLAY | 214 |
| MEASURING EACH IRIS POSITION IN EACH FRAME OF THE CAPTURED VIDEO IMAGES TO IDENTIFY MOVEMENT OF THE IRIS, AND IF IN ANY PLURALITY OF SEQUENTIAL FRAMES EITHER IRIS CHANGES POSITION, NYSTAGMUS IS IDENTIFIED AND THE SUBJECT FAILS THE TEST | 216 |

NORMAL HORIZONTAL GAZE: SMOOTH PURSUIT

ABNORMAL HORIZONTAL GAZE: SMOOTH PURSUIT

DRUG SCREENING DEVICE FOR MONITORING PUPIL REACTIVITY AND VOLUNTARY AND INVOLUNTARY EYE MUSCLE FUNCTION

CROSS REFERENCE TO RELATED APPLICATION

The current application claims priority to and the benefit of U.S. Provisional Patent Application Ser. No. 62/093,559 filed on Dec. 18, 2014, entitled "SYSTEM WITH A DRUG SCREENING DEVICE FOR MONITORING PUPIL REACTIVITY." This reference is hereby incorporated in its entirety.

FIELD

The present embodiments generally relate to a drug screening device for monitoring pupil reactivity and voluntary and involuntary muscle movement of the eyes of subjects.

BACKGROUND

A need exists for an easy to use, scientifically accurate drug screening device that can photograph, measure, and store images, pupil diameter data and iris images for a wide range of subjects and compare pupil diameters and irises to known ranges to determine if a subject has been using a neurologically impairing or a cognitively impairing substance.

A need exists for an easy to use, non-invasive, scientifically accurate and rapid drug and chemical screening device that can be used with a wide range of subjects to capture still and moving images of the right and left irises and pupils of a subject. The device can then compare images taken in real time against previous images, all captured under exacting conditions to determine if that subject has been using or has been exposed to any substance known to depress the central nervous system.

A need exists for a quick screening device, less than 5 minutes, for testing individuals that are exposed to grease, radiator fluid, deicing agents, dry cleaning chemicals, and commercial solvents which are identified by the US Environmental Protection Agency as known agents that depress the central nervous system of an individual.

The present embodiments meet these needs.

BRIEF DESCRIPTION OF THE DRAWINGS

The detailed description will be better understood in conjunction with the accompanying drawings as follows:

FIGS. 6A and 6B depict a diagram of the microprocessor and data storage usable with the drug screening device and system according to one or more embodiments.

FIG. 7 depicts an exemplary sequence of steps to perform a method of the invention according to one or more embodiments.

Figure 1:
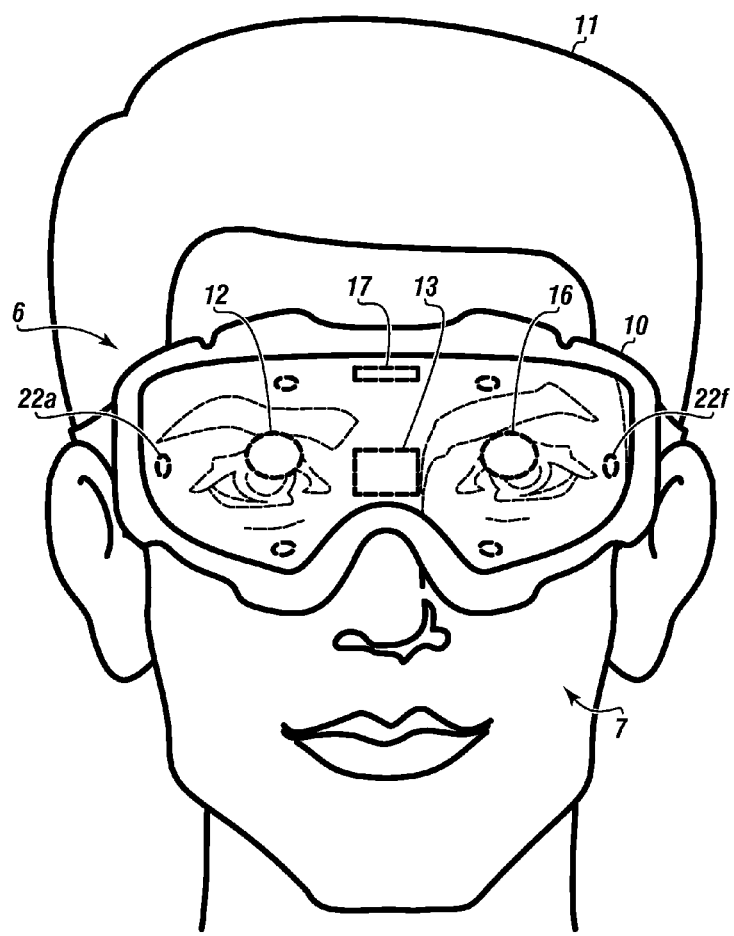
FIG. 1 depicts a front view of a drug screening device according to one or more embodiments.

The present embodiments are detailed below with reference to the listed Figures.

DETAILED DESCRIPTION OF THE EMBODIMENTS

Before explaining the present apparatus in detail, it is to be understood that the apparatus is not limited to the particular embodiments and that it can be practiced or carried out in various ways.

The present embodiments generally relate to a drug screening device for monitoring pupil reactivity and voluntary and involuntary eye muscle movement.

The embodiments also relate to a device for screening individuals for drug use, wherein the drug use can have a neurological effect that interferes with the normal functioning of the voluntary muscles of the eye and for testing and documenting the presence of nystagmus.

The human eye, with all its intricacies, is a very simple machine. It has several sets of muscles, voluntary sets that control movement of the eyeball vertically and horizontally, and two involuntary sets that control dilation and constriction of the iris, which affects pupil size. These muscles, both voluntary and involuntary, are controlled by the central nervous system. In a normal state, the muscles in the iris automatically respond bilaterally to changes in light intensity. The apparent simplicity of the involuntary functions of the eyes makes them very precise, reliable, and therefore predictable. The working of the eye is so reliable in fact that medical science has proven that when the eye does not react as expected, it is the result of head trauma (pupils appear to react independently of one another), disease, or a substance (drugs, alcohol, or exposure to toxic industrial chemicals) that depresses the central nervous system.

The device can determine if a subject is currently under the influence of a substance affecting the central nervous system.

It is of particular importance in that it takes approximately 15 minutes to 20 minutes for alcohol to reach the brain via the blood stream and cause impairment but more time for it to enter the urine. It takes 30-40 minutes after ingestion to reach maximum blood alcohol concentration. It is also important now that marijuana is legal for medical and/or recreational use in many states.

It is especially valuable in that THC and THC metabolites may remain in the body up to 3 weeks, but are only actively depressing the central nervous system for a maximum of 4 hours; few, if any, tests can quickly determine if the detected THC and THC metabolites are in fact active or if they are residues of past experiences with the drug. Hence, current testing methods and even those that detect and measure blood, urine, or CO2 levels of THC and or THC metabolites cannot provide conclusive evidence of physical impairment resulting from marijuana use.

In embodiments, the device can be a binocular device for screening individuals for drug use.

The invention can use a protocol with a database of baseline images, collected data, and results from prior testing, to compare with tests in real time to determine that: A) a subject's identity can be confirmed via iris matching using pattern recognition; B) the subject's right and left pupil sizes are the same and therefore, there is no evidence of medical or opthalmological malady; C) the subject's iris and pupil size is appropriate to the lumen output (brightness of ambient light); and D) the subject can successfully pass the horizontal gaze nystagmus stable gaze and smooth pursuit tests.

The device and method can address the need for a rapid, noninvasive testing procedure that can accurately determine if a subject is currently under the influence of marijuana, alcohol or another chemical substance that depresses the central nervous system or if the subject has a medical condition that may make that subject unfit to perform tasks that could prove harmful to themselves, other persons, vehicles, equipment, or property.

In embodiments, a binocular device can be used for screening individuals for drug use, alcohol use, or chemical exposure wherein the subject exhibits an observable and measurable neurological manifestation of uncontrollable horizontal tremor of the voluntary muscles of the eye, a condition called horizontal gaze nystagmus.

A benefit of the invention is that it can be quick and easy to use.

Another benefit of the invention is that it is noninvasive

Another benefit of the invention is that it can provide immediate documentation of the involuntary and voluntary reflexes of the eyes of a subject.

A further benefit of the invention can be that it can identify subjects that could cause motor vehicle or equipment accidents, physical, verbal, or emotional abuse, or damages and liabilities from human errors due to physical or cognitive impairment resulting from substance abuse or toxic chemical exposure.

The invention can be used to test both irises for use of a drug, alcohol, or exposure to a chemical known to have a neurological effect that interferes with normal functioning of the iris and the voluntary muscles of the eye.

The invention can test eyes and document reactivity of the iris under known light conditions and for the presence of horizontal nystagmus.

By capturing still and video images in color or infrared frequencies, the invention measures each pupil diameter.

Using the still and video images the identity of a subject, using an iris pattern recognition model, can be confirmed.

By using video images and examining the position of the irises in the frames, the presence of nystagmus can be determined.

The system and method can provide multiple alarms. For example, one alarm of the system can be an alarm notifying an administrator when one eye pupil diameter of a subject exceeds or falls below an opposite eye pupil diameter for the same subject.

The following definitions are used herein.

The term "administrative data storage" used herein can refer to a non-transitory computer readable medium, such as a hard disk drive, solid state drive, flash drive, tape drive, and the like. The term "non-transitory computer readable medium" excludes any transitory signals but includes any non-transitory data storage circuitry, e.g., buffers, cache, and queues, within transceivers of transitory signals. The administrative data storage contains computer instructions to instruct the administrative processor to do various tasks, for example: (i) companies to create and save accounts, (ii) individuals to create and save accounts, (iii) receive and save all eye baseline images, (iv) to receive any eye images written to it from a drug screening device described herein, and (v) to save and track test results of individual employees, contractors, or agents.

The term "administrative processor" used herein can refer to a computer or combination of processors, such as cloud processors, which receive information from the individual drug screening devices and save the information into a database of individuals.

The term "alarm" used herein can refer to an audio signal that can connect to a speaker on the frame, a flashing light on the frame, or spelled out on the LCD display, that can indicate that the frame is not positioned properly on the face of the subject. It can also refer to any notification by any electronic means to communicate information, such as through an email or text message.

The term "baseline images" as used herein can refer to the images in a library of baseline color eye images stored in the data storage. The library of baseline color eye images depicts a plurality of pupils of a plurality of subjects and indicates which light intensity and light source can be used to take the image. It can also include infrared eye images depicting the pupil and iris of a subject that can be stored in the library of baseline infrared eye images. The library of baseline infrared eye images can depict a plurality of pupils and irises from a plurality of subjects and also indicate the date the image was taken, which light intensity, and which Kelvin color temperature was used to measure the diameters of the pupils and any testing anomalies.

The term "camera" as used herein can refer to an image capture device used to capture digital images of the eyes that are either static or video images in color and/or infrared and stored in a microprocessor or a data storage of the invention or data storage on a network.

The term "central nervous system" used herein can refer to all structures of the brain and the spinal cord of a human being.

The term "data storage" used herein can refer to a non-transitory computer readable medium, such as a hard disk drive, solid state drive, flash drive, tape drive, and the like. The term "non-transitory computer readable medium" excludes any transitory signals but includes any non-transitory data storage circuitry, e.g., buffers, cache, and queues, within transceivers of transitory signals.

The term "facility" as used herein can refer to an administrative location for monitoring the administrative processor.

The term "frame" as used herein can refer to the housing portion of the invention which can contain some components and can have an imaging compartment for displaying tracking targets while simultaneously photographing a subject's eyes. The frame can also shield the eyes of a subject from extraneous light in order to ensure consistent lighting conditions under which the test is performed. The frame can consist of a molded plastic which can be from 4 inches to 8 inches in height, which can be from 12 inches to 14 inches wide, and 10 inches to 14 inches deep. The frame can be made from a lightweight washable composite material. The frame can be made from a bimetal that can be coated with a flexible or inflatable frame that softly cushions the face of the subject.

The term "horizontal gaze nystagmus test" (HGN) as used herein can refer to a test deemed to be scientific and reliable by The National Highway Safety Administration to determine the probability of a subject's intoxication or impairment when the subject attempts to follow a target on a horizontal plane and exhibits oscillation of the eyes or inability to smoothly track the target.

The term "human machine interface (HMI)" as used herein can refer to a thin film touchpad or keypad and a digital display. In embodiments, the HMI can be a graphic user interface or a graphic template that can both enable subject input and provide subject test results and movements of the eyes of the subject. In embodiments, the human machine interface can be real time streaming video images. The human machine interface can be configured to allow a user to input their identity and then search in a data base of the microprocessor to confirm the user's identity. In additional embodiments, the human machine interface can incorporate biometric readers.

The term "image" as used herein can refer to any graphic representation, illustration, picture, or photograph.

The term "iris" as used herein can refer to the circular diaphragm forming the colored portion of the eye and containing a circular opening, the pupil, in its center.

The term "light meter" as used herein can refer to a device that can both detect and measure the amount of ambient light in the chamber between the camera lens and the subject's pupil.

The term "LED" as used herein can refer to a light emitting diode.

The term "liquid crystal display" (LCD) as used herein can refer to a light emitting element that projects a white light and the brightness of the light is controlled by software.

The term "log file" as used herein can refer to a computer database file containing images and recorded data for eyes of a known subject.

The term "lumen output" as used herein can refer to a measure of the magnitude or intensity of light in a contained area.

The term "metabolites" as used herein can refer to products and byproducts of metabolism.

The term "microprocessor" as used herein can refer to a computer, such as a laptop connected to the frame.

The term "nystagmus" as used herein can refer to arrhythmic, oscillating motions of the eye.

The term "pupil" as used herein can refer to the opening in the middle of the iris of an eye through which light enters. The size of the pupil is an involuntary response to light of small muscle fibers in the iris that are controlled by the central nervous system.

The term "pupil reactivity" as used herein can refer to the reaction and response of the pupils to known and varying light conditions.

The term "smooth pursuit" as used herein can refer to the ability of a subject to control the muscles of the eye to continuously and closely follow an object across a horizontal visual field.

The term "stable gaze" as used herein can refer to the ability of a subject to control the muscles of the eye and maintain a stationary position while focusing on a target.

The term "standard baseline image" as used herein can refer to an image that at the specific lumen output and Kelvin color has previously been determined to exhibit the clearest and most well differentiated pupils and iris, a benchmark against which all subsequent images can be measured and imaging conditions can be repeated.

The term "subject failure protocol" as used herein can refer to known rules and procedures to follow as established by the organization administering the tests of the drug screening device when a subject fails the test.

The term "substances" as used herein can refer to any chemical introduced into the body by any means including but not limited to drugs, alcohol, solvents, intoxicants (such as marijuana/THC), opiates, or any chemical or chemical compound that may impact or impair the central nervous system.

The term "system" as used herein can refer to all devices, software, sensors, monitors, hardware, software, and processes used to integrate the parts of the device.

The phrase "tactile sensors" as used herein can refer to devices that contact with the face of the subject to detect contact with the frame.

The term "THC" as used herein can refer to tetrahydrocannabinol that is a compound derived from *cannabis* or produced synthetically and is the primary intoxicant in marijuana and hashish.

The term "tracking target" as used herein can refer to an image, which can be an object of focus, presented to the subject in the form of a stationary or animated image for the eyes of the subject to follow.

In embodiments, the drug screening device can use a frame, which can be made from molded plastic that can contain electronics and an opaque, flexible, rubberized material that can conform to the face, such as the material used in ski goggles. The frame can be wearable or table mounted. In additional embodiments, the frame can be light enough to attach to a wall. In additional embodiments, the drug screening device can weigh from 1 pound to 10 pounds.

The drug screening device can have subject identification input hardware attached to the frame or embedded into the frame.

Subject identification input hardware can be used to activate the drug screening device and identify the subject and locate previous or baseline images of the subject's eye(s). In embodiments, the drug screening device can be a magnetic card reader, bar code scanner, or a simple human machine interface (HMI).

In embodiments, a magnetic card reader can attach to the frame and can connect to a power source. Exemplary magnetic card readers and software can be those made by MAGTEK™ of Seal Beach, Calif.

In embodiments, a barcode scanner can be embedded into the frame and can connect to a power source. Exemplary barcode scanners, such as Model # MS-1 can be those made by MICROSCAN SYSTEMS™ of Renton, Wash.

In embodiments, a simple human machine interface (HMI) can be embedded into the frame and can connect to a power source. The human machine interface (HMI) can be a thin film touchpad or keypad and digital display. Exemplary touchpad and/or keypad with displays can be those made by ANAHEIM AUTOMATION™ of Anaheim, Calif.

The drug screening device can include a light source, which can be connected to a power supply and attached to the frame.

In embodiments, the power supply can be a battery. The battery can be direct current (DC). The battery can be a 10.8V Lithium-Ion 6-Cell Battery from AXIOM MEMORY SOLUTIONS™ of Irvine, Calif. In embodiments, the battery can be a 12V dry cell battery.

In embodiments, the power supply can be a plug that engages an AC wall circuit. In further embodiments, the power supply can be a rechargeable battery.

In embodiments, the light source can be a light emitting diode. In additional embodiments, the light source can be a liquid crystal display.

The light source can maintain color consistency at the full range of lumen output.

The light emitting diode can project either white light or infrared light. In embodiments, the frequency of the light emitting diode can be dimmable and can range from 105 lm@350 mA to 189 lm@700 mA. Usable light emitting diodes can be LUXEON REBEL™ model number LXML-PW51 made by PHILIPS LUMILEDS LIGHTING COMPANY™ of San Jose, Calif.

The liquid crystal display can project a white light. In embodiments, the brightness of the display can be controlled through software. An exemplary liquid crystal display can be model # NHD-16032BZ-FSW-GBW made by NEWHAVEN DISPLAY INTERNATIONAL™ of Elgin, Ill.

In embodiments, at least one camera can be used in the drug screening device. The at least one camera can be focused on at least one eye of a subject. The at least one camera can capture color, infrared, or both color and infrared frequencies. In additional embodiments, the at least one camera can capture video as well as images.

In embodiments, the infrared camera can be either a video image or a static image camera. Usable cameras can be those made by FLIR SYSTEMS™ of Wilsonville, Oreg.

In embodiments, the camera can be digital. The camera can connect to a power supply and can attach to the frame.

The device can include a partition disposed between the camera, the light source, and the face of a subject.

In embodiments, the partition can be made from plastic. The partition can be the height of the frame or 10 percent less in height than the frame. The partition can be the width of the frame or 10 percent less in width than the frame. In embodiments, the partition can have a thickness from 0.25 mm to 2 cm. In additional embodiments, the partition can be made from custom etched poly(methyl methacrylate) (PMMA), which is a thermoplastic, such as PLEXIGLAS® of Arkema, France.

In embodiments, the partition can be perforated allowing a camera lens of a camera to penetrate the partition, the light source to project light through the partition, or combinations thereof.

In embodiments, one to four perforations can be used. In embodiments, additional perforations can be used to allow airflow through the partition.

In embodiments, one perforation can have a diameter of 3 inches wide and can be rectangular or elliptical in shape. In other embodiments, the perforations can be circular with a minimum diameter of 0.5 of a centimeter to a maximum diameter of 2 centimeters. In further embodiments, the perforations can be square with a minimum width of 0.5 of a centimeter to a maximum width of 2 centimeters.

In embodiments, the perforation can be a slit extending from 10 percent to 98 percent of the width of the partition. In additional embodiments, some perforations can be smaller or some perforations can be larger in diameter than other perforations.

In embodiments, the liquid crystal display can be attached to or embedded in the partition.

In embodiments, the partition can have an image printed on or etched into or displayed on the partition enabling the subject to focus on the image at a known distance from the eye of the subject.

The image can be any image, such as a target, a bull's eye, an X, or a dot.

In embodiments, the image can be 0.75 of an inch high by 1 inch wide. The image can be something for the subject to focus on during the measurement of the pupil or pupils.

The measurement time can be very fast, typically 2 minutes or less.

The drug screening device can use at least four tactile sensors for determining correct positioning of frame on the face of the subject. The sensors can be sensors made by MICROCHIP TECHNOLOGIES™ of Chandler, Ariz. In embodiments, each sensor can connect to a microprocessor.

In embodiments, the tactile sensors can connect to a power supply. The sensors can be mounted on the frame or embedded in the frame. The tactile sensors can be located where the frame meets the face of the subject to detect excessive leakage of light from outside of the frame to the pupil of the subject being measured.

The drug screening device can use a light meter to detect the amount of ambient light in the chamber between the pupil of the eye and the lens of the camera. The light meter can connect to a microprocessor. An exemplary light meter can be those made by EXTECH INSTRUMENTS™ of Nashua, N.H.

In embodiments, the light meter can connect to a power supply. The light meter reading can be used to determine power output necessary to reproduce the lumen output level of a previous scan.

The drug screening device can include a microprocessor, which can be connected to the power supply, the sensors, the light meter, the camera(s), the wireless communication hardware, the speaker hardware, and combinations thereof. The microprocessor can have both on-board and external data storage. Exemplary microprocessors can be those made by INTEL™.

The microprocessor and the data storage can both be attached to the frame or embedded in the frame.

The microprocessor can include computer instructions to provide several alarms. The microprocessor can be configured to perform several functions.

A first function can be to monitor lumen output from the target display as measured by the light meter and control lumen output from the target display to provide consistent test conditions within the frame.

A second function can be to capture an image of at least one eye with the camera forming a captured image.

A third function can be to measure and store diameters of a pupil of the captured image for each eye forming a pair of measured diameters for the pupils.

A fourth function can be to compare the measured diameters of the pupils to each other to determine if the measured diameters can be equal and eliminate a diagnosis for the subject of a neurological or ophthalmic medical condition.

A fifth function of the microprocessor is to apply a pattern recognition model to the captured image and match an iris of the eye of the captured image to a stored image of the eye to confirm the identity of the subject.

A sixth function can be to perform a horizontal gaze nystagmus test to identify the presence of nystagmus by: capturing a plurality of directional sequences of video images of each iris and pupil of each eye of the subject for a minimum of 3 seconds at a minimum of 24 frames per second (FPS) while the subject focuses on and follows an animated target image initially moving horizontally across the target display from either a left to a right or from a right to a left.

A seventh function can be to measure the iris positions on each frame of the captured frames and if in any plurality of sequential frames the iris has not moved, nystagmus is present and the subject fails the test.

An eighth function can be to perform a stable gaze nystagmus test to identify the presence of nystagmus: by capturing a plurality of video images of each iris and pupil of each eye of the subject for a minimum of 3 seconds at a minimum of 24 frames per second while the subject focuses on a still image on an extreme margin of the target display.

A ninth function can be to measure each iris position in each frame of the captured video images to identify movement of the iris, and if in any plurality of sequential frames either iris changes position, nystagmus is identified and the subject fails the test.

The microprocessor can be configured to calibrate the target display within the frame to known light frequencies to ensure accuracy and repeatability of the tests.

In the drug screening device, the partition can include an image for focusing the at least one eye of the subject on the image of the partition at a known distance from the at least one eye of the subject.

In embodiments, a light source can be attached to the frame to illuminate a pupil of a subject and wherein the light source and target display can be calibrated by the microprocessor.

In embodiments, the drug screening device can use an administrative processor with an administrative data storage connected to a wireless network communication device, card, or chip that can communicates with the microprocessor. The administrative data storage can contain computer instructions to instruct the administrative processor to: present a human machine interface to an administrative display; receive information from the presented human machine interface to identify a subject; locate a drug screening record for the subject; and turn on and turn off the drug screening device.

In embodiments, the microprocessor can provide an alarm of at least one of: a device not the touching face alarm; turn off equipment alarm, and a notification alarm.

In the data storage of the microprocessor can be (a) computer instructions to instruct the microprocessor to perform self-test of maximum and minimum lumen outputs of the light source, (b) computer instructions to instruct the microprocessor to locate previous records of the subject stored in a data storage of the microprocessor, and/or (c) computer instructions to instruct the microprocessor to increase or decrease light output from the light source to a lumen level of a previous iris scan of the subject stored in a data storage of the microprocessor.

In embodiments, a plurality of cameras can be mounted to the frame. Each camera can focus on one eye or both eyes.

The drug screening device can include a method for assessing the capability of a person to operate heavy equipment.

The microprocessor as used herein, can include computer instructions to provide multiple different kinds of alarm, one of the alarms is a "device not touching face" alarm to the person operating the device which can be an audio signal or a visual signal on the display. The "device not touching face alarm" can be an alarm when one or more sensors do not detect touch of the subject's face to the frame. The "device not touching face" alarm can be a message to the subject of the test indicating that the subject needs to focus on the target of the display and follow the moving object with their eye(s).

In embodiments, the "device not touching face" alarm can be a message that the test is inconclusive. The "device not touching face" alarm can take the form of an email message, a text message, a voice phone call, an audio signal that connects to a speaker on the frame, or a flashing light on the frame, that indicates that the frame is not positioned properly on the face of the subject.

In embodiments, a "turn off equipment" alarm can be a command to a piece of external equipment or transportation device from the microprocessor to not turn on or operate because the subject of the test failed the test.

The "turn off equipment alarm" can take the form of a visual or an auditory warning, wired or wireless electronic or digital message, e.g., such as a text message or an email. The turn off equipment alarm may be a phone call or computer instructions to a connected electronic device or external piece of equipment, computer, data storage or microprocessor which controls the operation of the connected electronic device or external piece of equipment.

In embodiments, a "notification" alarm can be used to contact a supervisor or administrator about test parameters and test results for the drug screening device.

For example, a "notification" alarm can indicate that the subject has failed the test because one or both pupils are moving during a stable gaze nystagmus test.

In embodiments, another "notification" alarm can specifically indicate that a subject failed the test because the iris matching failed using the pattern recognition model and the subject's identification can't be confirmed.

In additional embodiments, another "notification" alarm can indicate that the device fails a self-test because the light source cannot be guaranteed as a consistent light with consistent lumen output.

A library of baseline color eye images can be stored in the data storage. The library of baseline color eye images depicts a plurality of pupils of eyes of a plurality of subjects and indicates which light intensity and light source can be used to take the image.

A library of baseline infrared eye images depicting a pupil of an eye of a subject can be stored in the data storage. The library of baseline infrared eye images can depict a plurality of pupils of eyes from a plurality of subjects and also indicates which light intensity and which light source was used.

Turning now to the Figures, FIG. 1 shows a front view of the drug screening device according to one or more embodiments.

In embodiments, the drug screening device can be wearable and in other embodiments, the drug screen device can be table or bench mounted devices.

The drug screening device 6 can have a light source 12, which can be connected to a power supply, which can be DC or AC.

In embodiments, the light source 12 can be mounted to a frame 10.

A light meter 17 can be attached to the frame 10. The light meter 17 can measure ambient light between a subject 11 and the frame 10.

A camera 16 can be mounted to the frame 10 and directed at one or both eyes of the subject 11.

At least one of a plurality of tactile sensors 22a-22f can be mounted to the drug screening device 6 for detecting if the frame is fitting against the face 7 of a user.

A target display 13 can be mounted to a partition that displays a still image and a subsequent animated target image to the eyes.

The target display 13 can be connected to the power supply.

The target display 13 can be mounted to the partition disposed between the camera 16 and the light source 12. The target display 13 can be a material capable of receiving and or projecting both a stationary and moving image for the subject 11 to focus on with their eye. The target display 13 can be a liquid crystal display or another monitor capable of providing a target image for the eye of the subject.

Figure 2:
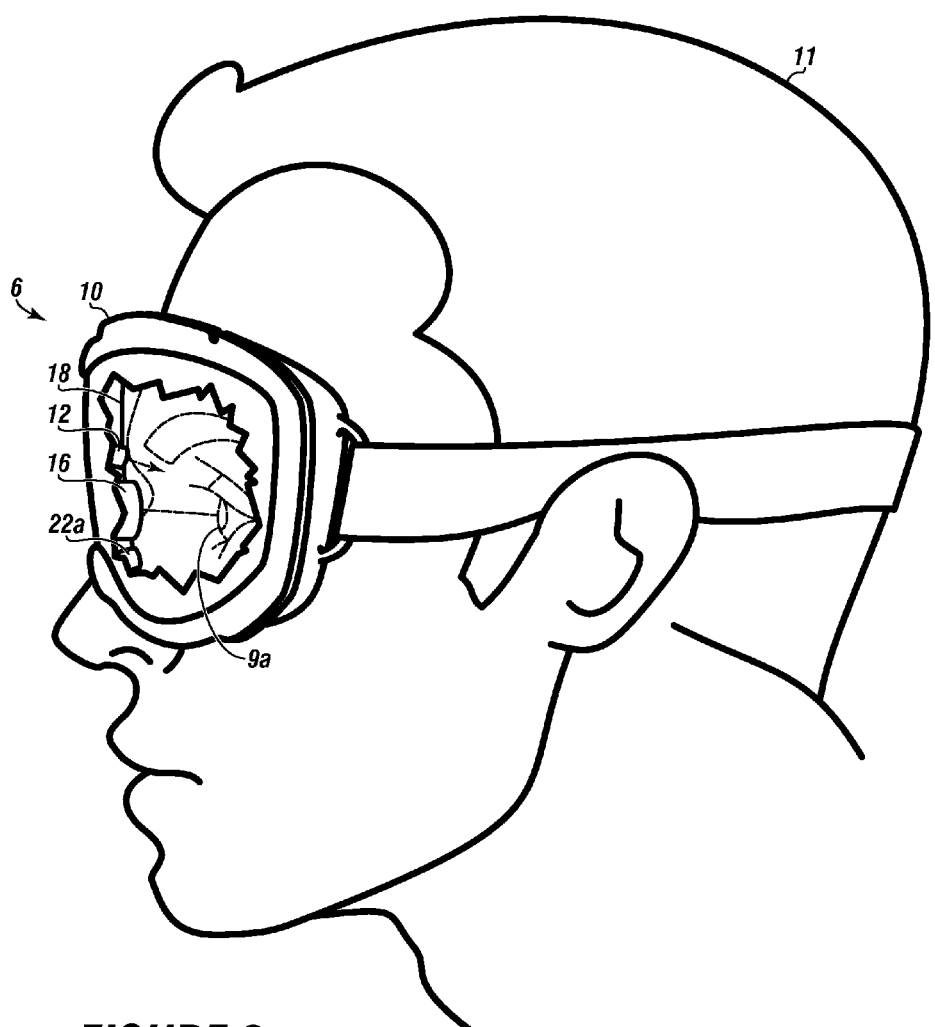
FIG. 2 depicts a side view with partial cut away of a drug screening device according to one or more embodiments.

FIG. 2 is a side view with partial cut away of the drug screening device according to one or more embodiments.

The drug screening device 6 is shown worn by the subject 11. In other embodiments, the drug screening device 6 can be a bench mounted model or a frame that is free standing, such as on a counter.

The camera 16 is shown and configured to focus on at least one eye 9a of the subject 11. The camera 16 can be attached or mounted to the frame 10.

A partition 18 can be depicted separating the camera 16 and a light source 12 and from the at least one eye 9 of the subject 11.

The at least one of a plurality of tactile sensors 22a are shown mounted to the frame 10 for measuring distance from the frame to the at least one eye of the subject.

Figure 3:
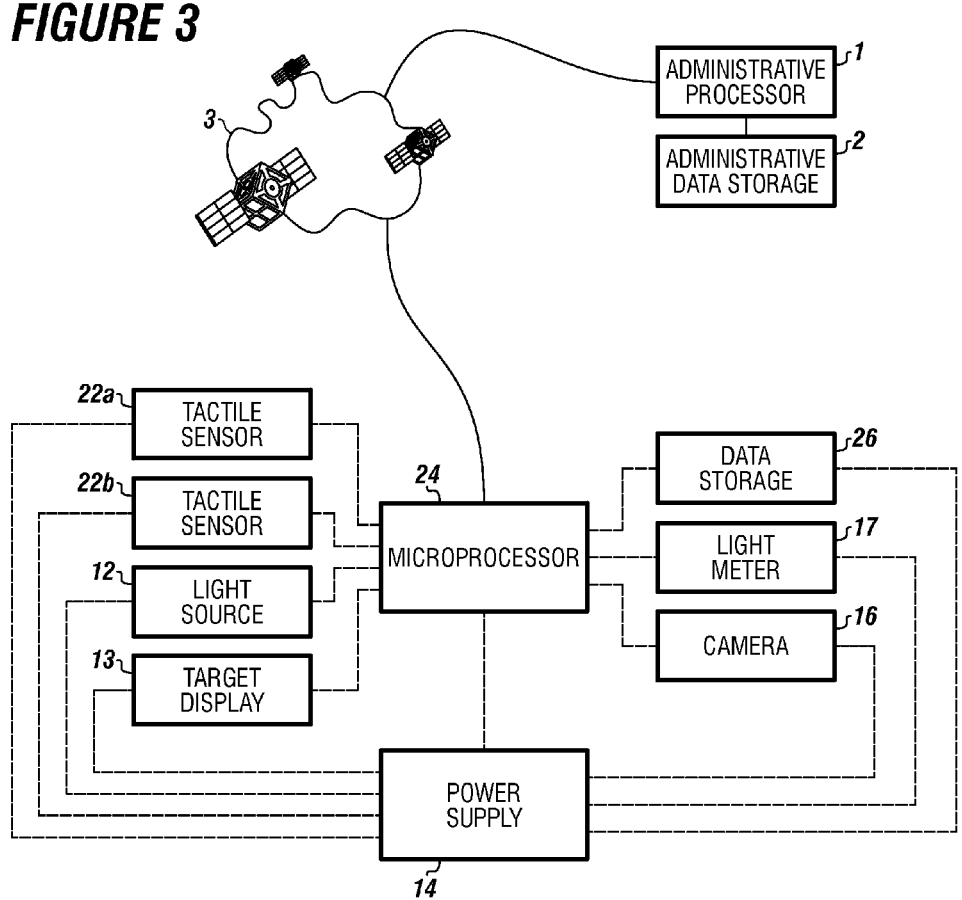
FIG. 3 depicts a diagram of the electronics usable with a drug screening device according to one or more embodiments.

FIG. 3 shows a diagram of a system using the drug screening device according to one or more embodiments.

The drug screening device can be used with an administrative processor 1 connected to an administrative data storage 2, which can communicate via a network 3 to a microprocessor 24, which can be mounted to the frame of the drug screening device.

In embodiments, the microprocessor 24 can be connected to a power supply 14.

In embodiments, the microprocessor 24 can be connected to and in communication with the light source 12, the target display 13, the camera 16, the light meter 17, the at least one of a plurality of tactile sensors 22a and 22b, and the data storage 26 for the microprocessor 24.

The power supply 14 can be in communication with the light source 12, target display 13, the camera 16, the light meter 17, the at least one of a plurality of tactile sensors 22a and 22b, and the data storage 26.

The network 3 can be a satellite network, the internet, a cable connection, a local area network, a wide area network, another global communication system or combinations thereof.

The administrative processor can be a computer, a laptop, a tablet, a server with a processor contained therein; a cloud based processing system, or another device known in the industry capable of two way communication.

Figure 4:
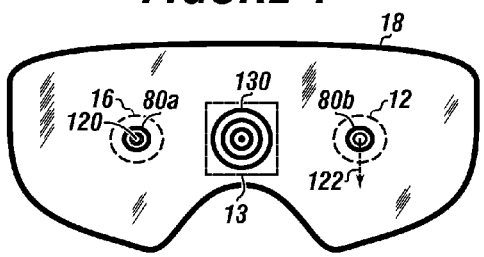
FIG. 4 depicts a detailed view of a partition of a drug screening device according to one or more embodiments.

FIG. 4 is a detailed view of a partition of the drug screening device according to one or more embodiments.

The partition 18 allows the camera lens 120 of the camera 16 to have a clear line of sight to at least one eye of the subject.

The partition 18 can have perforations 80a and 80b. Each perforation 80a and 80b can be configured to receive either a camera lens 120 of the camera 16 or a light 122 from the light source 12.

An image 130 is shown for focusing the at least one eye of the subject emanating from the target display 13. The image 130 on the partition can be located at a known distance from the at least one eye of the subject.

Although a bull's eye is shown as the image 130, the image 130 can be of any design, diagram, or representation.

Figure 5:
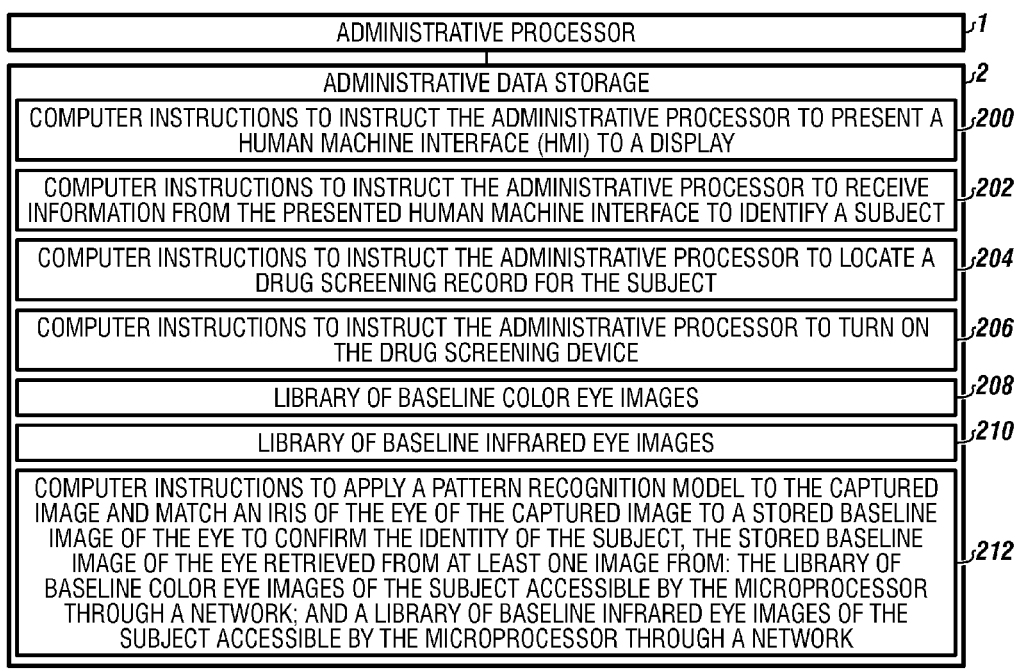
FIG. 5 depicts a diagram of an administrative processor and administrative data storage usable with the drug screening device according to one or more embodiments.

FIG. 5 depicts a diagram of an administrative processor and administrative data storage usable with the drug screening device according to one or more embodiments.

The administrative data storage 2 can contain computer instructions 200 to instruct the administrative processor 1 to present a human machine interface (HMI) to a display.

The administrative data storage 2 can contain computer instructions 202 to instruct the administrative processor 1 to receive information from the presented human machine interface to identify a subject.

The administrative data storage 2 can contain computer instructions 204 to instruct the administrative processor 1 to locate a drug screening record for the subject.

The administrative data storage 2 can contain computer instructions 206 to instruct the administrative processor 1 to turn on the drug screening device.

The administrative data storage 2 can contain a library of baseline color eye images 208.

The administrative data storage 2 can contain a library of baseline infrared eye images 210.

In the administrative data storage 2 can contain computer instructions 212 to instruct the administrative processor 1 to apply a pattern recognition model to the captured image and match an iris of the eye of the captured image to a stored baseline image of the eye to confirm the identity of the subject, the stored baseline image of the eye retrieved from at least one image from: the library of baseline color eye images of the subject accessible by the microprocessor through a network; and a library of baseline infrared eye images of the subject accessible by the microprocessor through a network.

FIGS. 6A and 6B depict a diagram of the microprocessor and data storage usable with the drug screening device and system according to one or more embodiments.

A data storage 26 can be in communication with a microprocessor 24.

The data storage 26 can contain computer instructions 30 to instruct the microprocessor to activate the drug screening device.

The data storage 26 can contain computer instructions 31 to instruct the microprocessor to monitor lumens output emitted from the target display as measured by the light meter and control lumens output from the target display to provide consistent test conditions within the frame.

The data storage 26 can contain computer instructions 32 to instruct the microprocessor to calibrate the target display to known light frequencies.

The data storage 26 can contain computer instructions 33 to instruct the microprocessor to capture an image of at least the right eye and the left eye with the camera forming a captured image.

The data storage 26 can contain computer instructions 34 to instruct the microprocessor to measure diameters of a pupil of the captured image for each eye forming a pair of measured diameters for the pupils.

The data storage 26 can contain computer instructions 35 to instruct the microprocessor to compare the measured diameters of the pupils to each other to determine if the measured diameters are equal and eliminate a diagnosis for the subject of a neurological or ophthalmic medical condition.

The data storage 26 can contain computer instructions 37 to instruct the microprocessor to perform a smooth pursuit horizontal gaze nystagmus test to identify the presence of nystagmus by: capturing a plurality of directional sequences of video images of each iris and pupil of each eye of the subject for a minimum of 3 seconds at a minimum of 24 frames per second (FPS) while the subject focuses on and follows an animated target image initially moving horizontally across the target display from either a left to a right, or from a right to a left and to measure the iris positions on each frame of the captured frames and if in any plurality of sequential frames the iris has not moved, nystagmus is present and the subject fails the test.

The data storage 26 can contain computer instructions 39 to instruct the microprocessor to perform a stable gaze nystagmus test to identify the presence of nystagmus: by capturing a plurality of video images of each iris and pupil of each eye of the subject for a minimum of 3 seconds at a minimum of 24 frames per second (FPS) while the subject focuses on a still image on an extreme margin of the target display and to measure each iris position in each frame of the captured video images to identify movement of the iris, and if in any plurality of sequential frames either iris changes position, nystagmus is identified and the subject fails the test.

The data storage 26 can contain computer instructions 41 to instruct the microprocessor to provide an alarm of at least one of: "a device not touching face" alarm; a "turn off equipment" alarm, and a "notification" alarm.

The data storage 26 can contain computer instructions 42 to instruct the microprocessor to perform self-test of maximum and minimum lumen outputs and color temperatures of the light source.

The data storage 26 can contain computer instructions 44 to instruct the microprocessor to locate previous records of the subject stored in data storage of the microprocessor.

The data storage 26 can contain computer instructions 50 to instruct the microprocessor to increase or decrease light output from the light source and/or target display to a lumen level of a previous iris scan of the subject stored in a data storage of the microprocessor.

FIG. 7 depicts an exemplary sequence of steps to perform a method of the invention according to one or more embodiments.

The method can include monitoring lumen output emitted from the target display as measured by the light meter and control lumen output from the target display to provide consistent test conditions within the frame, as shown in step 200.

The method can include capturing an image of at least the right eye and left eye with the camera forming a captured image, as shown in step 202.

The method can include measuring diameters of a pupil of the captured image for each eye forming a pair of measured diameters for the pupils, as shown in step 204.

The method can include comparing the measured diameters of the pupils to each other to determine if the measured diameters are equal and eliminate a diagnosis for the subject of a neurological or ophthalmic medical condition, as shown in step 206.

The method can include applying a pattern recognition model to the captured image and match an iris of the eye of the captured image to a stored image of the eye to confirm the identity of the subject, the stored image of the eye retrieved from at least one image of: a library of baseline color eye images of the subject accessible by the microprocessor through a network; a library of baseline infrared eye images of the subject accessible by the microprocessor through a network, as shown in step 209.

The method can include performing a horizontal gaze nystagmus test to identify the presence of nystagmus by: capturing a plurality of directional sequences of video images of each iris and pupil of each eye of the subject for a minimum of 3 seconds at a minimum of 24 frames per second (FPS) while the subject focuses on and follows an animated target image initially moving horizontally across the target display from either a left to a right, or from a right to a left, as shown in step 211.

The method can include measuring the iris positions on each frame of the captured frames and if in any plurality of sequential frames the iris has not moved, nystagmus is present and the subject fails the test, as shown in step 213.

The method can include performing a stable gaze nystagmus test to identify the presence of nystagmus: by capturing a plurality of video images of each iris and pupil of each eye of the subject for a minimum of 3 seconds at a minimum of 24 frames per second (FPS) while the subject focuses on a still image on an extreme margin of the target display, as shown in step 214.

The method can include measuring each iris position in each frame of the captured video images to identify movement of the iris, and if in any plurality of sequential frames either iris changes position, nystagmus is identified and the subject fails the test, as shown in step 216.

Figure 8A:
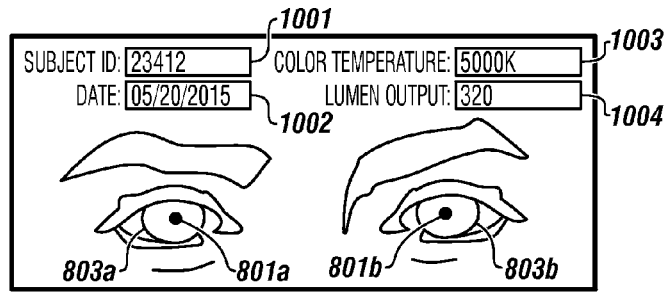
FIGS. 8A-8C depict stored database images of a subject's right and left eyes, pupils, and irises at different light settings captured by a drug screening device according to one or more embodiments.
Figure 8B:
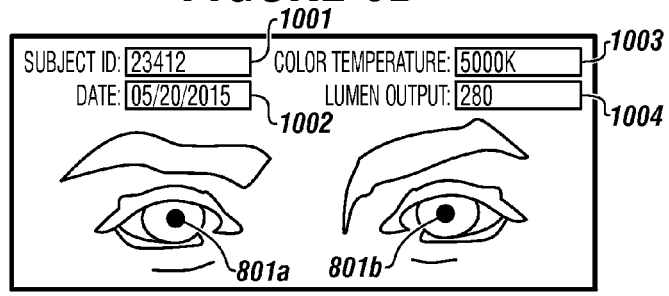
Figure 8C:
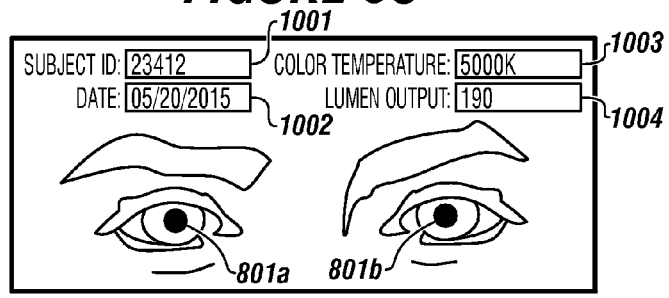

FIGS. 8A-8C depict stored database images of a subject's right and left eyes, pupils, and irises at different light settings captured by a drug screening device according to one or more embodiments.

In embodiments, these Figures depict 3 out of a possible 30, stored "baseline" database images of a subject's right and left eyes, pupils and irises, at different lumen output settings. These eyes are photographed 30 times under different lighting conditions to approximate all the possible pupil sizes that the subject might encounter.

FIG. 8A depicts a pair of pupils 801a and 801b and a pair of iris 803a and 803b which are in "normal configuration." The normal configuration would be a first standard baseline image for photographing the eyes under these specified lighting conditions.

A field can be provided to indicate a subject ID 1001, shown as 23412.

A field can be provided to indicate a date an image was recorded 1002, shown as 05/20/2015.

A field can be provided to indicate a color temperature 1003, shown as 5000K.

A field can be provided to indicate the lumen output 1004, which is depicted as 320.

FIG. 8B depicts a pair of pupils 801a and 801b for the same subject but under different lighting conditions with a different lumen output.

The subject ID 1001 is shown as 23412. The date 1002 is shown as 05/20/2015. The color temperature 1003 is shown as 5000K. The lumen output 1004 is shown as 280.

FIG. 8C depicts a pair of pupils 801a and 801b of the same subject but under additionally different lighting conditions with a different lumen output.

The subject ID 1001 is shown as 23412. The date 1002 is shown as 05/20/2015. The color temperature 1003 is shown as 5000K. The lumen output 1004 is shown as 190.

At subject intake, the subject's eyes are photographed multiple times, once each at various lumen outputs. The photographs can then be stored in the library of baseline color eye images and/or the library of baseline infrared images for that subject. The photographs can become the subject's baseline images. Among the photographs, one image will show the clearest and most well defined irises and pupils of the eyes of the subject and that image can be deemed the standard baseline image against which all subsequent images are compared. During testing, the drug screening device can capture an image at the same lumen output as the standard baseline image. The drug screening device will compare the images using a pattern recognition model and attempt to obtain a match. If a match fails, the drug screening device will attempt to find a match with any of the remaining images in the database. If a match can be found, subject identification can be confirmed. If a match is found with any image other than the standard baseline image, the drug screening device will register a pupil reactivity anomaly.

Figure 9A:
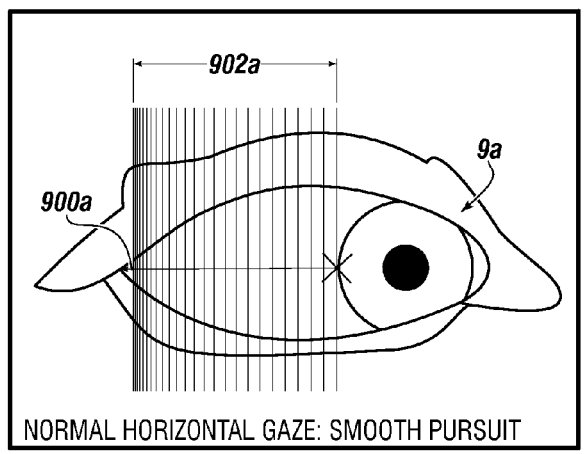
FIGS. 9A and 9B depict a graphical depiction of two different results from performing a horizontal gaze nystagmus test to identify a smooth pursuit according to one or more embodiments.
Figure 9B:
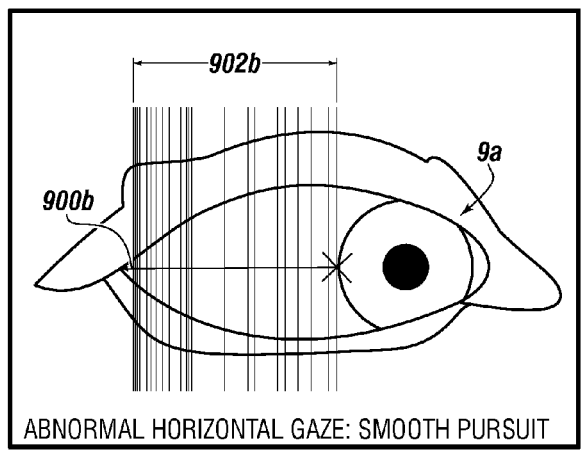

FIGS. 9A and 9B depict a graphical depiction of two different results from performing a horizontal gaze nystagmus test to identify the presence of nystagmus in the eyes.

FIG. 9A depicts a first tracking path 900a for at least one eye 9a showing a normal horizontal gaze: a smooth pursuit.

A first tracking distance 902a at 24 frames per second (FPS) is shown.

Horizontal nystagmus, an uncontrollable oscillation of the eye along the horizontal axis of the eye, is a symptom of intoxication, drug use or exposure to high levels of chemical substances responsible for depressing the central nervous system which affects the optic nerve and the voluntary and involuntary muscles of the human eye. Under the influence of any such chemicals, nystagmus will prevent the subject from being able to smoothly pursue or follow a tracking target. As a result, the video frames describing the presence of nystagmus will show the iris of the eye failing to progress in a plurality of sequential frames, followed by an apparent leap forward to another location along the tracking path.

FIG. 9B depicts a second tracking path 900b for the at least one eye 9a showing an abnormal horizontal gaze: smooth pursuit test where the at least one eye performs a halting progress and a smooth progress is clearly disrupted.

A second tracking distance 902b at 24 frames per second (FPS) is also shown.

Figure 10A:
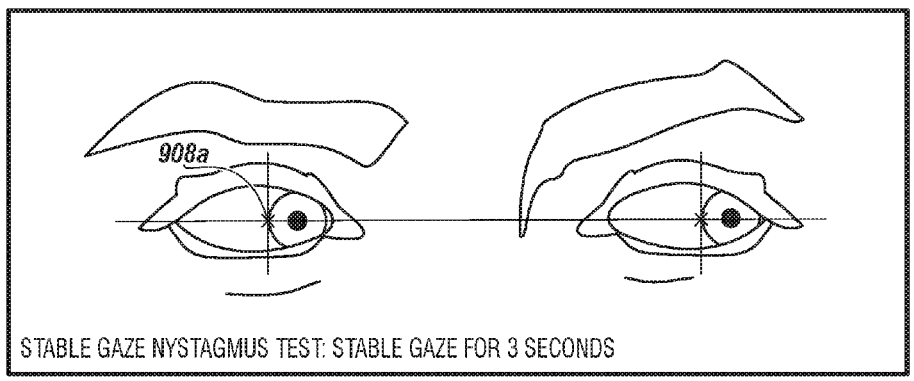
FIGS. 10A and 10B depict a graphical depiction of two different results from performing a stable gaze nystagmus test with the system and method according to one or more embodiments.
Figure 10B:
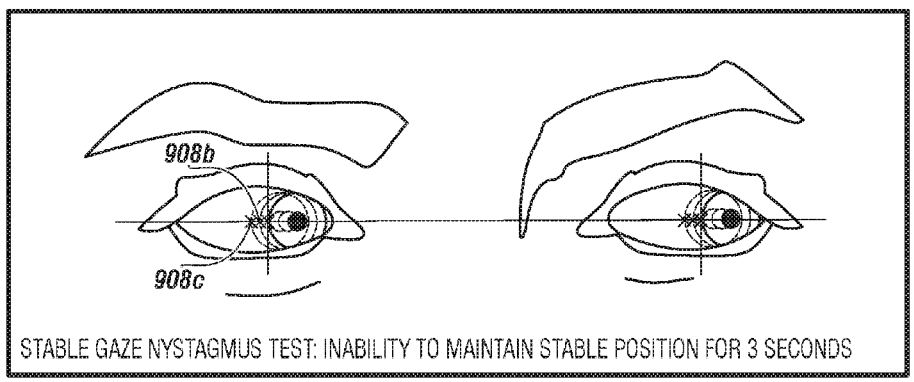

FIGS. 10A and 10B depicts a graphical depiction of results identifying a stable gaze nystagmus test.

A graphical depiction of competency and incompetency of maintaining stable gaze in a horizontal gaze nystagmus test is shown.

Stable gaze nystagmus testing provides further proof of the presence of nystagmus. The test can be performed by having the subject focus on a stationary tracking target positioned to the extreme right or left on the display. When nystagmus is present, the subject's irises will be unable to remain at rest and over the course of time, a plurality of video frame sequences will show the irises oscillating along a horizontal axis into and from the corner of the eye.

FIG. 10A depicts a measured result of a normal sustained gaze for a subject of 3 seconds is shown. At least one element of a plurality of elements 908a (the "x" on both a vertical axis and horizontal axis simultaneously) shows no movement during the full 3 seconds of the test and that the subject passes the test.

FIG. 10B depicts that a subject can have an inability to maintain a stable gaze for 3 seconds under a stable gaze nystagmus test. At least one element of a plurality of elements 908b and 908c (the two different "x" notations show that the "x" has moved on the horizontal axis) depict eye movement during the full 3 seconds and that the subject fails the test.

To further explain the invention, a subject, Smith, inputs his ID into the drug screening device and then places his face into the frame such that all the tactile sensors register a positive response.

The frame fits his face such that the subject's eyes are enclosed within the imaging compartment containing the display and the camera.

The microprocessor locates Smith's files among the stored images in the data storage at the facility and A) creates a new log file for Smith; and B) sets the lumen output to the same lumen output of Smith's designated standard baseline image. Smith can be instructed to focus on a static image on the display.

The camera captures and the microprocessor saves the image of Smith's eyes to the log file. The microprocessor takes a measurement of the right and left pupil diameters from the captured image and compares the two. If they do not match, the microprocessor initiates a pupil matching test.

Because a pupil size mismatch may be normal for Smith, the microprocessor searches through all of Smith's baseline images to find any images with pupil diameters the same sizes as those in the captured image. If none can be found, Smith fails the test and the sequence is terminated.

The microprocessor can simultaneously send a notification alarm to the facility or directly to a supervisor or administrative representative to take appropriate action and a notification alarm to Smith instructing him to follow a subject failure protocol.

The microprocessor can record a pupils working in concert "fail" in the log file. The microprocessor can save the log file to the administrative data storage at the facility. If a matching image is found, the microprocessor records a pupils working in concert "known anomaly."

The microprocessor can apply a pattern recognition model to the irises of the eyes on the captured image and attempts to match the irises from the found image. If the irises do not match, Smith's identity cannot be confirmed and Smith fails and the sequence is terminated.

The microprocessor can simultaneously send a notification alarm to the facility or directly to a supervisor or administrative representative to take appropriate action and a notification alarm to Smith instructing him to follow a subject failure protocol.

The microprocessor can record an identity confirmed "fail" in the log file. The microprocessor can save the log file to the administrative data storage at the facility. If a match is found and the matching image is not the standard baseline image, the microprocessor can record a pupil reactivity "error" in the log file.

Because anomalous pupil reactivity is always symptomatic of drug use or chemical exposure when actively depressing the central nervous microprocessor, but not in itself conclusive evidence of intoxication, the microprocessor initiates horizontal gaze nystagmus tests. Smith is instructed to focus and follow a stationary tracking target positioned on the right or leftmost vertically centered locus on the display.

The camera captures video images at a minimum of 24 frames per second for a minimum of 3 seconds. The microprocessor saves the video to the administrative data storage at the facility.

The microprocessor scans the frames and if in a plurality of random sequential frames the iris position changes, the microprocessor records stable gaze nystagmus "present; #", wherein # represents the number of sequences found in which the iris had moved.

The microprocessor then initiates a smooth pursuit test. Smith is once again instructed to follow the tracking target. The camera captures video images of Smith's eyes following the tracking target as it moves in a straight horizontal line from its original location across the entire width of the display and then back again. The microprocessor saves the video to the administrative data storage at the facility.

The microprocessor scans at the individual frames and if in any plurality of sequential sets of 5 or more frames the iris does not move, then the microprocessor records smooth pursuit nystagmus "present; #", wherein # represents the number of sequences in which the iris was stationary.

If nystagmus is present in both horizontal gaze nystagmus tests, the microprocessor can simultaneously send a notification alarm to the facility or directly to a supervisor, administrative or human resources representative to take appropriate action and a second notification alarm to Smith instructing him to follow a subject failure protocol. The microprocessor saves the log file to the administrative data storage at the facility. If Smith fails only one of the horizontal gaze nystagmus tests, the failed test is repeated.

If Smith fails the test a second time, the microprocessor can simultaneously send a notification alarm to the facility or directly to a supervisor, administrative or human resources representative to take appropriate action and a second notification alarm to Smith instructing him to follow a subject failure protocol. The microprocessor saves the log file to the administrative data storage at the facility.

A subject, Jones, inputs her ID into the drug screening device then places her face into the frame such that all the tactile sensors register a positive response.

The frame fits the face such that the subject's eyes are enclosed within the imaging compartment containing the display and camera.

The microprocessor locates Jones' files among the stored images in the administrative data storage at the facility then A) creates a new log file for the subject, and B) sets the lumen output to the same lumen output of Jones' designated standard baseline image.

Jones is instructed to focus on a static image on the display. The camera captures an image and the microprocessor saves the image of Jones' eyes into the log file. The microprocessor takes a measurement of the right and left pupil diameters from the captured image and compares the two and if they match, indicating that the muscles in her irises are working normally.

The microprocessor records pupils working in concert "pass" in the log file. The microprocessor initiates a pupil diameter matching test.

The microprocessor searches through Jones' entire baseline images to find any images with pupil diameters the same sizes as those in the captured image. The microprocessor finds a match with Jones' standard baseline Image. The microprocessor records a pupil reactivity "pass" into the log file.

The microprocessor applies a pattern matching model to the irises of the eyes on the captured image and attempts to match the irises from Jones' standard baseline image. The irises match and Jones' identity is confirmed. The microprocessor writes an identity confirmed "pass" in the log file.

The microprocessor then initiates stable gaze nystagmus tests. Jones is instructed to focus and follow a stationary tracking target positioned on the right or left most vertically centered locus on the display. The camera captures video images at a minimum of 24 frames per second for a minimum of 3 seconds.

The microprocessor saves the video to the administrative data storage in the facility. The microprocessor looks at the frames and finds no sequential frames in which the iris position changes, the microprocessor writes a stable gaze nystagmus "pass" into the log file.

The microprocessor then initiates a smooth pursuit test. Jones is once again instructed to follow the tracking target on the display.

The camera captures video images of Jones' eyes following the tracking target as it moves in a straight horizontal line from its original location across the entire width of the display and then back again.

The microprocessor saves the video to the administrative data storage at the facility. If the microprocessor scans the individual frames and detects no frames in which the iris does not move then Jones passes the test.

The microprocessor then records a smooth pursuit "pass" into Jones log file. The microprocessor saves the log file to the administrative data storage at the facility.

Figure 11:
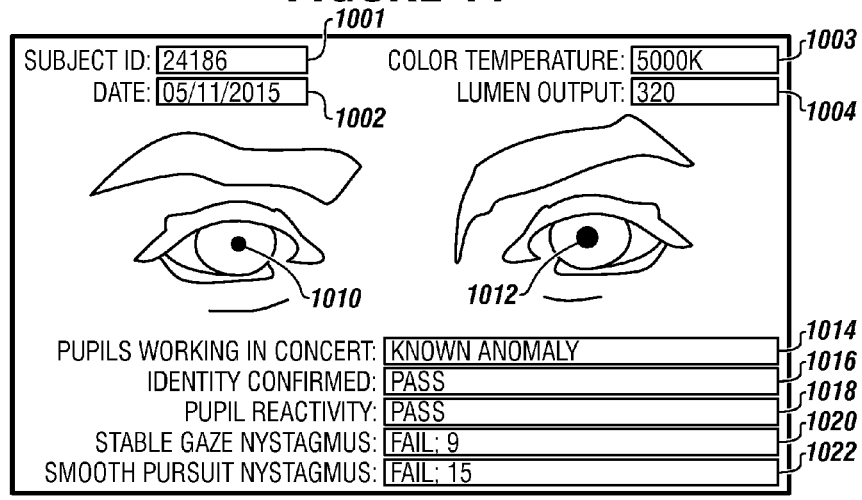
FIG. 11 depicts a graphical depiction of an exemplary log file entry from a drug screen device according to one of more embodiments.

FIG. 11 depicts a graphical depiction of exemplary log file entry from the drug screening device.

A typical log file can be created by the drug screening device.

A field can be provided in the log file to indicate a subject ID 1001, shown as 24186.

A field can be provided in the log file to indicate a date 1002 an image was recorded, shown as 05/11/2015.

A field can be provided in the log file to indicate a color temperature 1003, shown as 5000K.

A field can be provided in the log file to indicate a lumen output 1004, shown as 320.

A normal pupil 1010 is shown.

A dilated pupil 1012 is shown.

Element 1014 shows the results of pupils working in concert, which are indicated here as "known anomaly". This is only identifiable using the database of information about the subject form the administrative data storage.

Element 1016 shows the identity confirmed results shown here as "pass" which means the subject has had his identify confirmed by the drug screening device.

Element 1018 shows the results of pupil reactivity, which are indicated here as "pass."

Element 1020 shows results of a stable gaze nystagmus test as "fail; 9". The number 9 indicates the number of sequences of frames that the nystagmus is indicated in.

Element 1022 shows results of a smooth pursuit nystagmus test as "fail; 15." The number 15 indicates the number of sequences of frames that the nystagmus is indicated in.

While these embodiments have been described with emphasis on the embodiments, it should be understood that within the scope of the appended claims, the embodiments might be practiced other than as specifically described herein.

What is claimed is:

1. A drug screening device for identifying a subject with temporary neurological impairment resulting from a chemical that depresses a subject's central nervous system, the drug screening device comprising:
   a. a frame configured to fit flush with a face of the subject;
   b. a camera attached to the frame, the camera configured to focus simultaneously on at least one eye of the subject;
   c. a light meter configured to measure ambient light within the frame;
   d. a partition in the frame separating the camera from the at least one eye;
   e. a target display mounted to the partition displaying a still image and a subsequent animated target image to the at least one eye;
   f. at least one of a plurality of tactile sensors mounted to the frame configured to verify contact with the face to prevent extraneous light from entering the frame;
   g. a microprocessor with a data storage attached to the frame controlling the camera, receiving signals from the light meter, controlling the target display, and monitoring signals from the at least one of the plurality of tactile sensors;
   h. a power supply attached to the frame electrically connected to the camera, the light meter, the target display, the microprocessor and the at least one of the plurality of tactile sensors; and
   i. a light source attached in the frame to illuminate a pupil of the subject and wherein lumens of the light source and the target display are calibrated by the microprocessor.

2. The drug screening device of claim 1, wherein the microprocessor is configured to calibrate the target display within the frame to known light frequencies to ensure repeatability of a horizontal gaze nystagmus test and a stable gaze nystagmus test.

3. The drug screening device of claim 1, wherein the partition has an image printed, etched or displayed on the partition at a known distance from the at least one eye of the subject.

4. The drug screening device of claim 1, further comprising an alarm of at least one of: a device not touching face alarm, a turn off equipment alarm, and a notification alarm.

5. The drug screening device of claim 1, wherein the data storage of the microprocessor includes computer instructions in the data storage to instruct the microprocessor to perform a self-test of maximum and minimum on lumen output of the light source.

6. The drug screening device of claim 1, wherein the data storage of the microprocessor includes computer instructions in the data storage to instruct the microprocessor to increase or decrease light output from the light source to a lumen level of a previous iris scan of the subject stored in an administrative data storage.

7. The drug screening device of claim 1, further comprising a plurality of cameras mounted to the frame, and wherein each of the plurality of cameras can focus on an eye or both eyes.

8. The drug screening device of claim 1, wherein the data storage comprises a plurality of computer instructions to instruct the microprocessor to:
   a. activate the drug screening device;
   b. monitor lumen output emitted from the target display as measured by the light meter and control lumen output from the target display to provide consistent test conditions;
   c. calibrate the target display to known light frequencies;
   d. capture the image of eyes of the subject with the camera forming a captured image;
   e. measure diameters of the pupils of the captured image for both eyes of the subject forming a pair of measured diameters for the pupils;
   f. compare the measured diameters of the pupils to each other to determine if the measured diameters are equal and eliminate the diagnosis for the subject of a neurological or ophthalmic medical condition;
   g. perform a horizontal gaze nystagmus test to identify the presence of nystagmus;
   h. perform a stable gaze nystagmus test to identify the presence of nystagmus;
   i. provide an alarm of at least one of: a device not touching face alarm, a turn off equipment alarm, and a notification alarm; and
   j. perform a self-test of maximum and minimum lumen outputs and color temperatures for the light source.

\* \* \* \* \*